(12) United States Patent
Kopetsch et al.

(10) Patent No.: US 9,642,539 B2
(45) Date of Patent: May 9, 2017

(54) PIEZOELECTRIC SENSOR FOR MEASURING PRESSURE FLUCTUATIONS

(75) Inventors: Roland Kopetsch, Berlin (DE); Mohammad Nasseri, Berlin (DE); Stephan Bergmann, Berlin (DE)

(73) Assignee: SECTORCON INGENIEURGESELLSCHAFT FUR SYSTEM-UND SOFTWARETECHNIK MBH, Berlin (DE)

( * ) Notice: Subject to any disclaimer, the term of this patent is extended or adjusted under 35 U.S.C. 154(b) by 302 days.

(21) Appl. No.: 12/993,615

(22) PCT Filed: Jul. 17, 2009

(86) PCT No.: PCT/EP2009/005543
§ 371 (c)(1),
(2), (4) Date: Feb. 17, 2011

(87) PCT Pub. No.: WO2009/141171
PCT Pub. Date: Nov. 26, 2009

(65) Prior Publication Data
US 2011/0166459 A1 Jul. 7, 2011
US 2012/0065526 A9 Mar. 15, 2012

(30) Foreign Application Priority Data
May 20, 2008 (DE) .................. 10 2008 024 737

(51) Int. Cl.
A61B 5/02 (2006.01)
A61B 5/021 (2006.01)
(Continued)

(52) U.S. Cl.
CPC ............ *A61B 5/021* (2013.01); *A61B 5/0285* (2013.01); *A61B 5/02125* (2013.01);
(Continued)

(58) Field of Classification Search
CPC ....... A61B 5/02; A61B 5/02035; A61B 5/021; A61B 5/02116; A61B 5/02125;
(Continued)

(56) References Cited

U.S. PATENT DOCUMENTS 4,216,403 A 8/1980 Krempl et al.
4,413,202 A 11/1983 Krempl et al.
(Continued)

FOREIGN PATENT DOCUMENTS

DE 28 31 938 A1 8/1979
DE 34 24 536 A1 1/1986
(Continued)

OTHER PUBLICATIONS

ISA/EP; International Search Report for PCT/EP2009/005543; Jan. 7, 2010; 3 pages.

*Primary Examiner* — Jacqueline Cheng
*Assistant Examiner* — Puya Agahi
(74) *Attorney, Agent, or Firm* — Hahn Loeser & Parks, LLP

(57) ABSTRACT

The invention relates to a piezoelectric sensor for the improved measurement of mechanical variables such as force, pressure or measurement variables which are derived there from, particularly a PVDF film sensor having an improved sensitivity and temperature stability of the measurement signal for pressure measurements that vary in time and/or space, and for the one-and two-dimensional determination of the position and propagation velocity of pressure fluctuations and pressure waves with a single measurement sensor at a measurement location. A preferred field of application of the invention is the non-invasive, low strain and continuous measurement of the pulse rate and the systolic and diastolic blood pressure of humans and animals by determining the velocity and the signal form of the pulse (Continued)

waves. The object of the invention is to allow the measurements of the blood pressure and the pulse rate, for example even in the case of emergency patients having only a very low blood pressure and patients having circulatory disorders in the extremities, for example patients which have developed diabetes or the "smoker's leg", by using only one sensor at a measurement location due to the improved measurement sensitivity of the piezoelectric sensor, with the result that the continuous application of a pressurized jacket for continuously measuring and monitoring the blood pressure is not necessary. The present invention solves this problem in that a plurality of parallel strips of a piezoelectric material (1) are associated as a measurement membrane in the pressure sensor according to the invention with a sensor base body (4) in such a manner that the parallel strips are tension preloaded in a one-dimensional and elastic manner in the direction of the piezo dipole orientation and that an empty cavity (5) is provided between the tension preloaded piezoelectric sensor material (1) in the measurement portion and the sensor base body (4), formed by a recess/cutout.

6 Claims, 2 Drawing Sheets

(51) Int. Cl.

| | | |
|---|---|---|
| *A61B 5/0285* | (2006.01) | |
| *G01L 9/00* | (2006.01) | |
| *A61B 5/024* | (2006.01) | |
| *A61B 5/022* | (2006.01) | |
| *A61B 5/03* | (2006.01) | |
| *A61B 5/026* | (2006.01) | |

(52) U.S. Cl.
CPC ............... *G01L 9/008* (2013.01); *A61B 5/02* (2013.01); *A61B 5/022* (2013.01); *A61B 5/024* (2013.01); *A61B 5/026* (2013.01); *A61B 5/02035* (2013.01); *A61B 5/02116* (2013.01); *A61B 5/03* (2013.01); *A61B 2562/0247* (2013.01); *A61B 2562/043* (2013.01)

(58) Field of Classification Search
CPC ......... A61B 5/022; A61B 5/024; A61B 5/026; A61B 5/03
USPC .......................................... 600/485
See application file for complete search history.

(56) References Cited

U.S. PATENT DOCUMENTS

| | | | |
|---|---|---|---|
| 5,265,481 A | | 11/1993 | Sonderegger et al. |
| 5,494,043 A | | 2/1996 | O'Sullivan et al. |
| 5,501,111 A | | 3/1996 | Sonderegger et al. |
| 5,649,535 A | | 7/1997 | Voith |
| 5,840,036 A | | 11/1998 | Voith |
| 6,200,270 B1 | | 3/2001 | Biehl et al. |
| 6,237,398 B1 | * | 5/2001 | Porat et al. .................. 73/54.09 |
| 6,764,446 B2 | * | 7/2004 | Wolinsky et al. ............ 600/300 |
| 7,019,307 B1 | * | 3/2006 | Gribb et al. ............. 250/390.12 |
| 2005/0264133 A1 | * | 12/2005 | Ketterling ............. B06B 1/0692 310/311 |
| 2006/0179952 A1 | * | 8/2006 | Tavares et al. .................. 73/754 |
| 2006/0195035 A1 | * | 8/2006 | Sun ........................ A61B 5/021 600/503 |
| 2007/0049837 A1 | | 3/2007 | Shertukde et al. |
| 2007/0100332 A1 | * | 5/2007 | Paul .................... A61B 18/1492 606/41 |
| 2007/0113654 A1 | | 5/2007 | Carim et al. |
| 2007/0287923 A1 | * | 12/2007 | Adkins et al. ................ 600/485 |

FOREIGN PATENT DOCUMENTS

| | | |
|---|---|---|
| DE | 196 02 460 A1 | 8/1996 |
| DE | 195 42 019 C1 | 3/1997 |
| DE | 102 14 220 A1 | 10/2003 |
| EP | 0 370 203 A1 | 5/1990 |
| EP | 0 491 655 A1 | 6/1992 |
| WO | 0197691 A1 | 12/2001 |
| WO | 2005067387 A2 | 7/2005 |

* cited by examiner

PIEZOELECTRIC SENSOR FOR MEASURING PRESSURE FLUCTUATIONS

CROSS REFERENCE TO RELATED APPLICATIONS

This application is a national stage of PCT International application no. PCT/EP2009/005543 filed Jul. 17, 2009, which claims priority to German application Serial No. 10 2008 024 737.5 filed May 20, 2008.

BACKGROUND OF THE INVENTION

The invention relates to a piezoelectric sensor according to the preamble of patent claim 1 for an improved measurement of mechanical variables such as force, pressure or measurement variables which are derived there from, particularly a PVDF film sensor exhibiting an improved sensitivity and temperature stability of the measurement signal for measuring pressures that vary in time and/or space, and for the one- and two-dimensional determination of a position and propagation velocity of pressure fluctuations and pressure waves. A preferred field of application for the invention is a non-invasive, low impact and continuous measurement of a pulse rate and a systolic and diastolic blood pressure of humans and animals by measuring arterial pulse waves through a sensor configured with piezoelectric PVDF foils.

Through the oriented deformation of a piezoelectric material in a direction of a polarization, microscopic dipoles are formed by displacing negative and positive charge centers within the elementary cells. The summation over all elementary cells of the crystal leads to a macroscopically measurable electrical voltage, which is directly proportional to a deformation in a defined deformation range for a longitudinal deformation in a direction of a polarity.

Piezoelectric foils are typically made from polyvinylidenfluoride (abbrev. PVDF). A transparent, partially crystalline fluoride thermoplastic, which is polarized for producing the piezoelectric properties, this means it is heated, stretched in one dimension and thus exposed to a strong oriented electromagnetic field for orienting the dipoles. The piezoelectric properties thus created are highly directional through the monoaxial orientation. In order to discharge the dipole charges created during the deformations, the PVDF foil is metal coated. This metal coating is mostly made from gold or copper nickel alloys, vapor deposited on the foil. Thus, the charges can be tapped through electrodes at the edge of the piezoelectric foil and can be converted into a measurable electric current through a charge amplifier (charge-voltage converter).

BRIEF SUMMARY OF INVENTION

The human heart is a discontinuously feeding displacement pump and feeds blood in its contraction phase through arteries towards the peripheral blood vessels, from where it returns to the heart through the venous blood vessel system. The blood pressure spike in the aorta created during the contraction phase of the heart, thus is the systolic blood pressure, which essentially is a function of the heart function parameters, the blood pressure in the aorta at the output of the heart during its slacking phase is the diastolic blood pressure, which is substantially a function of the beat volume and elasticity of the aorta. A continuous long term monitoring of both blood pressure values is among other things required for detecting short blood pressure spikes is an important prerequisite for diagnosing in particular the vital functions and possible health risks of a patient. For the time being, this is only possible in an invasive manner through a blood pressure measuring canule or a blood pressure measuring catheter applied into the artery of the patient. The disadvantages of the invasive method besides discomfort the patient are the risk of infections and the risk of injury when the patient moves his arms. Furthermore, the method can only be used in a hospital.

Most known methods for non-invasive blood pressure measurement operate according to the Riva-Rocci method. A jacket typically applied to the upper arm of a patient is thus initially pumped up with air pressure, which is above the expected systolic blood pressure and has the consequence that the artery in the arm of the patient is compressed enough, so that the blood flow at this location of the artery is interrupted. The blood pressure in the jacket is now slightly lowered by opening a valve. When the jacket pressure falls below the systolic pressure, the blood flow in the blood vessel is reestablished in the contraction phase of the heart for a time period in which the arterial pressure is higher than the jacket pressure. However, since the interior cross section of the blood vessel is still very small, the level of turbulence increases due to the higher blood flow velocity at this location, so that an increased flow noise or a noise through the blood vessel movement in the rhythm of the heartbeat, the so-called Korotkoff noise, can be heard, e.g. through a stethoscope in blood flow direction shortly behind the blood vessel contraction during this time frame. Thus, the systolic blood pressure can be derived for this method from the jacket pressure that is readable during the slow jacket pressure lowering when the Korotkoff noise can be heard for the first time. Analogously thereto, the diastolic blood pressure can be derived from reading the jacket pressure at which the Korotkoff noise cannot be heard anymore for the first time when the reduction of the jacket pressure continues, since no blood vessel contraction occurs anymore below the diastolic blood pressure. An inverse sequence of the measurement steps is also possible by increasing the jacket pressure slowly from the bottom up. It is appreciated that an auscultatoric gap occurs for certain patients with high blood pressure, this means the Korotkoff noise disappears when lowering the pressure between the systolic and the diastolic pressure. When the pressure is lowered further, the noise reappears, and the diastolic pressure is determined when the Korotkoff disappears again.

A method of this type for non-invasive measurement of blood pressure is described in DE 34 24 536, in which an inflatable arm jacket includes a microphone for detecting the Korotkoff noises and the systolic and the diastolic blood pressure is determined and displayed through a digital processing unit. The measurement precision of this method in particular for determining the diastolic blood pressure is not very high, furthermore, it is not suitable for continuous blood pressure monitoring, since each measurement process takes a long time through the slow jacket pressure change and a more frequent repetition of the measurements than every five minutes leads to a measurement falsification. Furthermore, the patient is discomforted through the high jacket pressure and there is a risk of tissue damage at the application location.

Through another method, the blood pressure is measured in a non-invasive and continuous manner without using cumbersome compression jackets which discomfort a patient. Thus, the fact is being used that in particular, the systolic blood pressure correlates quite well with the propagation velocity of a pulse wave or the reciprocal of the pulse transition time in an artery of a human. Thus, P. Elter in his dissertation "Methods and systems for non-invasive continuous and non-discomforting blood pressure measurements" (University Karlsruhe 2001), analytically proves this relationship by deriving the relationship:

$$p=(2\rho/E_p)(R/h)c^2-E_o/E_p$$

As a hydraulic replacement model for the pulse wave propagation in an artery using an undamped wave and a flow without losses in an elastic hose, neglecting exterior forces like gravity, wherein p is the blood pressure in the artery, p is the blood density, R is the inner radius of the artery, h is the wall thickness of the artery, c is the pulse wave velocity, and $E_0$ and $E_p$ are empirical elasticity constants for describing the arterial wall thickness. Based on this model, the pressure can be determined from the pulse wave velocity alone presuming the ratio of the blood vessel sizes R and h to be constant:

$$p_{i\ cal}=C_1 *c_{i\ cal}^2 *C_2,$$

wherein $C_1$, $C_2$ are constants which can be determined e.g. through two individual calibration measurements i=1, 2 which have to be performed at different blood pressures, thus e.g. one measurement has to be performed at rest and one measurement has to be performed under a physical load. Furthermore P. Elter provides statistical evidence in his dissertation that the systolic blood pressure correlates with the propagation velocity of a pulse wave or the reciprocal of a pulse transition time.

Thus accordingly DE 10214220 describes a method and a device for non evasive low impact and continuous measurement of the pulse and the blood pressure by determining the pulse wave velocity. Thus, the measurement of the systolic blood pressure which typically discomforts the patient the most is performed by determining the pulse transition time through at least two pressure sensors preferably attached at the upper arm and the lower arm in particular based on piezo electric foils. The determined pulse transit times or systolic blood pressure values are stored in a processing unit. The measurement of the diastolic blood pressure is performed in particular according to the oscillometric method through an arm jacket which is only loaded with a pressure in the order of magnitude of the diastolic blood pressure which only causes minor discomfort for the patient and minor loading of the body tissue at the application location also for long term blood pressure monitoring. The two calibration measurements for systolic blood pressure determination through pulse transit time measurement are thus performed in an oscillometric manner through the arm jacket at the beginning of the measurement interval.

The associated disadvantages are that at least two pressure sensors are required at two measurement locations for determining the pulse transit time and that the measurement sensitivity is too low for the prior art pressure sensors based on piezo electric foils, in particular for patients with circulation problems in their extremities, e.g. for patients which suffer from diabetes or from a so called smoker's leg. For continuously measuring the diastolic blood pressure also here the permanent application of a pressure jacket is required for measuring according to the Riva-Rocci method. Additional disadvantages of the prior art pressure sensors based on piezo electric foils are bad temperature stability of the measurement data through the undefined and high heat flow in the sensor and bad measurement results through insufficient contact between the sensor surface and the irregularly shaped skin surface of a human.

EP 491 655 describes a force sensor system permanently installed in a pavement for measuring weights of vehicles, wherein piezo elements which are installed in a hollow profile are installed with an elastic preload. This preload is achieved in that the hollow profile is elastically opened through lateral clamping and the piezo elements thus can be inserted into the hollow profile. Thus, after releasing a clamped connection, a high vertical elastic pressure preloading of the piezo element occurs. Thus the preloading is neither performed through tension nor in a direction of the piezo-dipole orientation, so that the force sensor thus introduced is not subjected to any measurement sensitivity improvement in piezo-dipole direction through reduced influencing of the signal through the other effective components through the elastic preload.

EP 370 203 describes an acceleration sensor in which a piezo foil element is suspended above a base of a metal support component, wherein the base is preformed in a defined manner and used for the piezo foil to come in contact with the base under an acceleration that is high enough and thus prevents an expansion of the piezo foil that is too high. Thus, the piezo foil is not tension preloaded in a defined manner in piezo-dipole orientation and a cavity between the piezo foil and a support component is not used for the piezo foil to nestle against the cavity, e.g. for pressure wave detection at an uneven surface.

Thus, it is the object of the present invention to provide a pressure sensor based on piezo electric converters, in particular piezo electric foils through which measuring pressures that vary time based and/or spatially and deriving measurement variables there from is facilitated with a better measurement sensitivity.

Thus it is furthermore an object of the present invention to provide a pressure sensor based on piezo electric converters, in particular piezo electric foils, through which the measurement of pressures that vary time based and/or in a spatial respect and deriving measurement variables there from is facilitated with improved stability for the measurement data.

It is another object of the present invention to provide a pressure sensor based on piezo electric converters, in particular piezo electric foils in which the pressure sensor is skin friendly.

It is another object of the invention to provide a pressure sensor based on piezo electric converters, in particular piezo electric foils through which the position and the propagation velocity of pressure fluctuations and pressure waves and measurement variables that can be derived there from is facilitated with only one measurement sensor and only one measurement location.

It is another object of the present invention to provide a pressure sensor based on piezo electric converters, in particular piezo electric foils, through which the measurement of pressures which are variable time based or in a spatial respect and the measurement variables that can be derived there from is also facilitated from surfaces with an irregular shape like e.g. human skin with an improved measurement sensitivity.

It is another object of the present invention to provide a pressure sensor based on a piezo electric converters, in particular piezo electric foils through which the non invasive, impact free and continuous measurement and monitoring of the pulse frequency and of the systolic and the diastolic blood pressure is facilitated for a human and a animal without continuously applying a pressure loaded jacket for measurement according to a Riva-Rocci method.

According to the invention the object is accomplished through the piezo electric sensor according to the characterizing features of claim 1.

Advantageous embodiments of the invention are described by the characterizing features of the dependent claims.

Thus it is a core feature of the invention that the pressure sensor according to the invention includes a plurality of parallel strips made from a piezo electric material as a measurement membrane and associated with a sensor base element, so that the strips are preloaded with tension in a mono dimensional elastic manner in a direction of the piezo-dipole orientation and a free cavity is provided between the piezo electric sensor material mounted under tension in the measurement portion and the sensor base element through a recess or milled recess.

Through the mono dimensional elastic preload of the piezo electric sensor material through tension in a direction of the piezo-dipole orientation different measurement variables than the measurement variables to be measured are reduced in a direction of the dipole orientation due to the only minor influencing of the signals through the other effective components and thus the measurement precision of the sensor is increased. Thus, the strong directional orientation of the piezo electric materials through their mono axial orientation is used for improving measurement sensitivity in a controlled manner. Another improvement of the sensor measurement sensitivity is achieved through the plurality of parallel piezo electric sensor strips since in the data processing through the sensor controller only the measurement signals of the piezo electric sensor material strips are selected for data processing whose measurement signals are the best. Since an open cavity is provided between the piezo electric sensor material mounted under tension in the measurement area and the sensor base element, the temperature stability of the measurement data is improved through the reduced temperature flow of the sensor material to the sensor base element and the sensor material in the measurement area can nestle in an optimum manner against measurement surfaces which have an irregular shape, like e.g. human skin, which further improves sensor measurement sensitivity. Since the distance of the parallel piezo electric sensor material strips from one another is known, the position and propagation velocity of pressure fluctuations and pressure waves can be determined and measurement variables that can be derived there from can be determined with only one measurement sensor at only one measurement location perpendicular to the sensor material strips, like e.g. pulse wave velocity for animals and humans, or through calibration measurements also at another angle, where the measurement precision for a vertical arrangement of the sensor material strips relative to the pressure fluctuation propagation direction is the highest.

Thus, the result is that pressure sensors that are improved over the prior art are provided through the present invention based on piezo electric converters, in particular pressure sensors based on piezo electric foils for non invasive and low impact and continuous measurement of the pulse frequency and of the blood pressure through determining the arterial pulse wave velocity and the pulse wave signal form for animals and humans which are characterized by an improved measurement sensitivity and temperature stability of the measurement data and through which the determination of the position and the propagation velocity of pressure fluctuations and pressure waves and of the measurement variables derivable there from and the determination of the arterial pulse wave velocity and of the pulse wave signal form for humans and animals is facilitated at a measurement location with only one measurement sensor.

The permanent application of a pressure loaded jacket according to the Riva-Rocci-method is not required any more according to the invention. Through the improved measurement sensitivity of the sensor e.g. the blood pressure and the pulse frequency can be measured also for emergency patients with only very low blood pressure and for patients with circulation problems in the extremities, thus e.g. with patients who suffer from diabetes and the so called smoker's leg.

It is another advantage of the invention that the plurality of the piezo sensor strips on a sensor facilitates positioning the sensor, since it does not have to be positioned exactly at the location of the pressure fluctuation, like e.g. an artery, based on the measurement signal redundancy.

In an advantageous embodiment of the invention piezo electric foils, in particular metal coated polyvinylidenfluoride-foils (abbreviated PVDF-foils) are used as piezo electric converters of the pressure sensors.

In another advantageous embodiment of the invention the PVDF-foil of the pressure sensor is coated on its metal side with a protective foil and glued onto a flexible circuit board preferably made from polyimide as a measurement membrane laminate.

In another advantageous embodiment of the invention the sensor base element, onto which the measurement membrane laminate is applied with a tension through gluing, is configured as a bending stiff rigid support circuit board onto which the amplifier electronics of the piezo electric converter is soldered directly.

In another preferred embodiment of the invention two measurement membrane laminate layers disposed on top of one another, whose sensor material strip orientation relative to one another is preferably perpendicular, are being used in order to facilitate a two dimensional determination of the position and the propagation velocity of pressure fluctuations and pressure waves and measurement values that are derivable there from like the arterial pulse wave velocity for animals and humans for any directional orientation of the sensor at the measurement location.

In another advantageous embodiment of the invention portions of measurement membrane laminates whose sensor material arrangement is preferably perpendicular to one another are being used in order to facilitate a two dimensional determination of the position and the propagation velocity of pressure fluctuations and pressure waves and measurement values that are derivable there from like e.g. the arterial pulse wave velocity for animals and humans for any angular arrangement of the sensor on the measurement location.

Thus the object of the invention is achieved in their entirety through the provided piezo electric sensor.

BRIEF DESCRIPTION OF THE SEVERAL VIEWS OF THE DRAWINGS

Subsequently a preferred embodiment of the invention is described in more detail with reference to the appended drawing figure wherein.

DETAILED DESCRIPTION OF THE INVENTION

Figure 1:
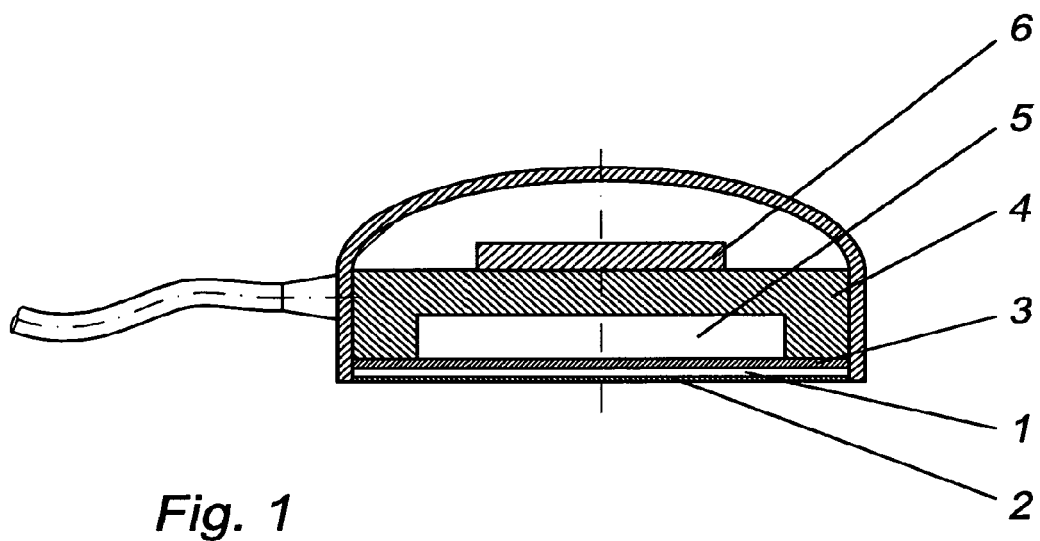
FIG. 1 illustrates a piezo electric sensor according to the invention in a sectional view.

FIG. 1 illustrates a sensor based element 4 in a cross sectional view, wherein the sensor base element is configured as a rigid support circuit board on which the electronic amplifier 6 (charge amplifier) is directly soldered in order to prevent charge losses. The measurement membrane laminate includes a flexible polyimide conductor plate 3, plural parallel metal coated PVDF-foils 1 and a polyimide protective foil 2 and is glued on the sensor base element 4, so that a cavity 5 is created between the measurement membrane laminate the sensor base element 4, wherein the cavity can be produced e.g. through milling the sensor base element-support circuit board 4 and so that the measurement membrane laminate is tension preloaded in a direction of the piezo polarization of the PVDF-foil strips 1. The amplifier electronics 6, the sensor base element support circuit board 4, the polyimide circuit board 3 and the metal side of the PVDF-foil strips 1 are connected in an electrically conductive manner through the electrodes and circuit board conductive paths which are not illustrated in further detail herein. The protective foil 2 protects the PVDF-foil strips against humidity and contamination and thus protects the metal electrodes against oxidation. This additionally provides good skin compatibility. The provided cavity 5 facilitates nestling the measurement membrane laminate at uneven surfaces like e.g. the skin of a human and thus improves measurement data quality. The cavity 5 furthermore reduces the heat flow between the PDVF foil strip 1 and the sensor base element-carrier circuit board 4 and renders the heat flow predictable, so that the temperature stability of the measurement data is improved.

Figure 2:
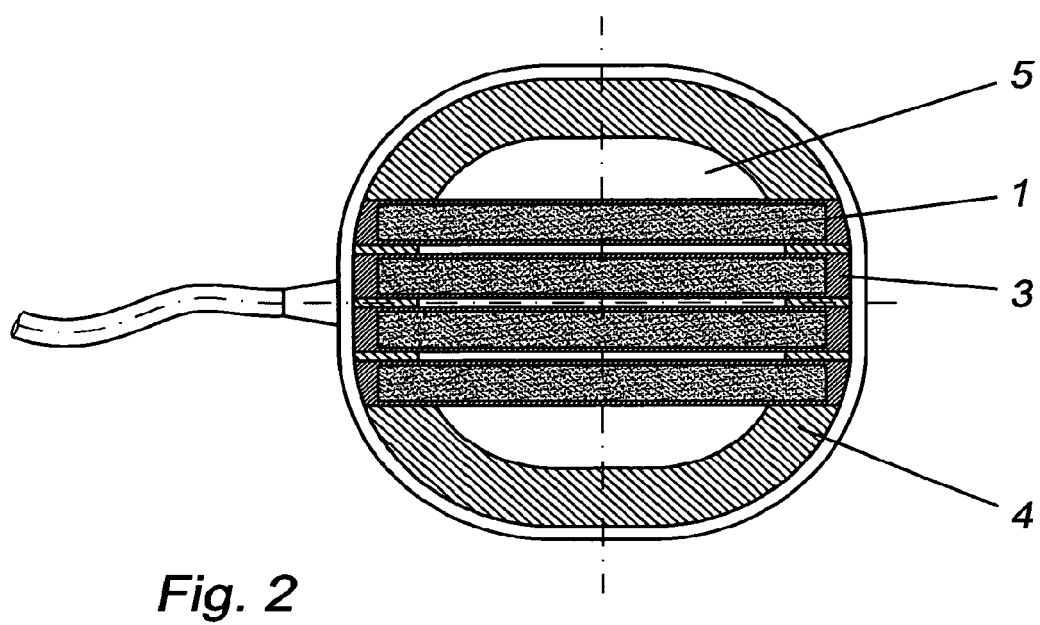
FIG. 2 illustrates a piezo electric sensor according to the invention in a bottom view.

FIG. 2 illustrates the four parallel PVDF-foil strips 1 in a bottom view, wherein the foil strips are glued onto the sensor base element 4 with a tension preload and are glued as a measurement membrane laminate onto the rigid carrier circuit board which is configured as a sensor base element 4 through forming a cavity 5 through milling.

Figure 3:
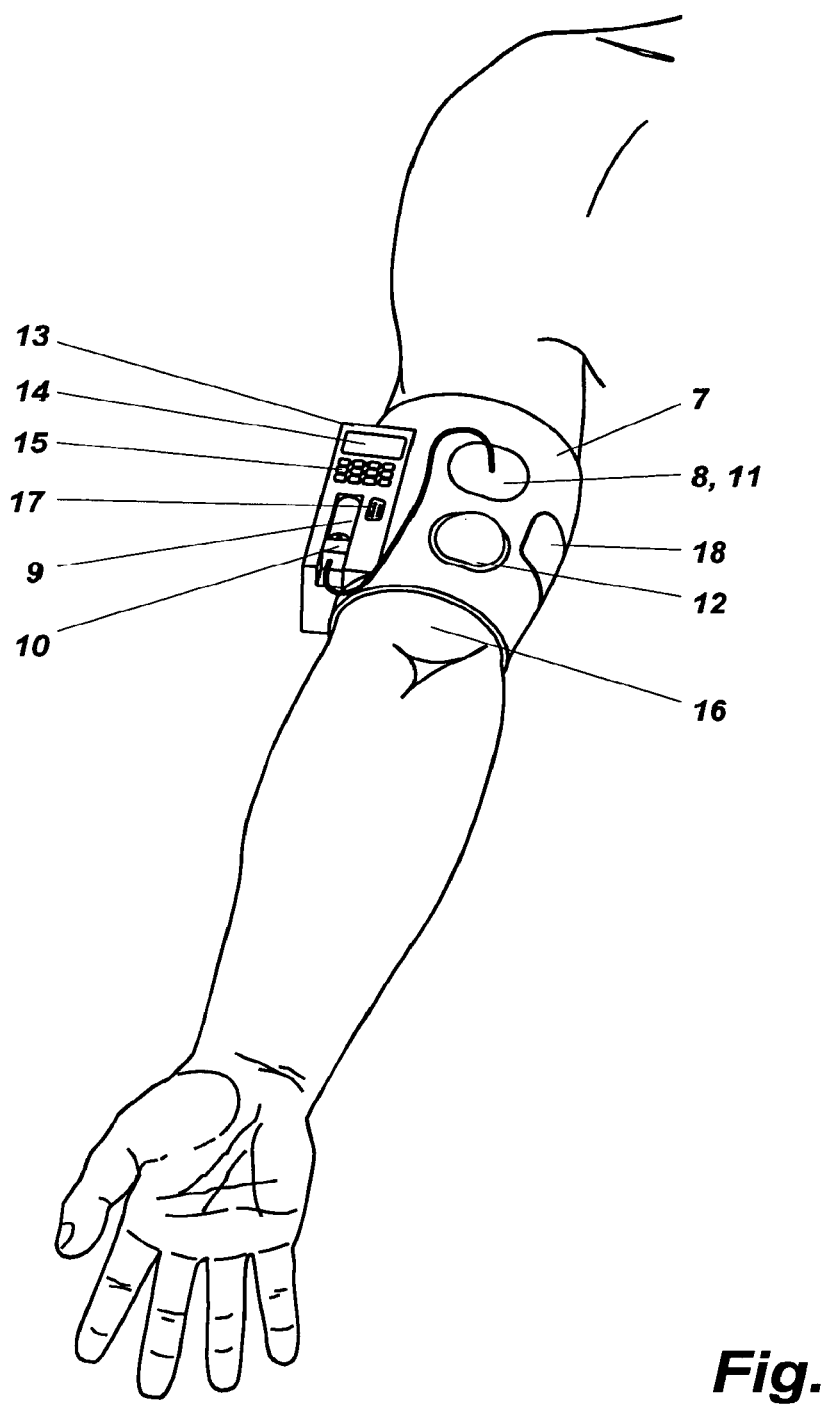
FIG. 3 illustrates a measurement and processing device according to the invention applied to an arm of a patient in a perspective view.

FIG. 3 illustrates the configuration of a device for non invasive low impact and continuous measurement and monitoring the blood pressure and pulse frequency of a human as an embodiment for a piezo electric sensor for pressure fluctuation measurement according to the invention. The upper arm 16 of a patient is enveloped by an arm jacket 7 that is closable through a loop and hook closure, wherein the jacket includes at least one pressure pillow 8 which is filled e.g. with a measurement liquid for calibrating the measurement of the diastolic and systolic blood pressure. The pressure cushion 8 is configured as an elastic membrane at the side oriented towards the skin. The arm jacket 7 furthermore includes a piezo electric pressure sensor according to the invention as a pulse wave sensor 12 which can be applied e.g. at the arm of the patient 16 in the area of an artery through respective application of the jacket 7 and which is made from plural parallel PVDF-piezo foil strips 1 which are glued onto a rigid support circuit board with directly integrated amplifier electronics 6 as a sensor base element 4 forming a cavity 5 between the PVDF-piezo foil 1 and the sensor base element 4, wherein the plural parallel PVDF-piezo foil strips 1 are glued onto the sensor base element 4 with a tension preload. The PVDF-piezo foil strips 1 are thus glued together with a polyimide protective foil and flexible polyimide circuit board to form a measurement membrane laminate. The propagation of a pulse wave in the artery generates an electric voltage signal in the PVDF-foil strips 1 of the pulse wave sensor 12 through expanding the piezo electric material, wherein the electric voltage signal is amplified in the amplifier electronics 6 and processed in the control and processing unit 13. From the phase shift of the pulse wave signals of the different parallel PVDF-foil strips 1 the pulse transit time is computed in the control and processing unit 13 and the systolic and diastolic blood pressure is computed from the pulse transit time and from the shape of the pulse wave signals. The display of the measurement values and the menu guidance is provided through an LCD foil 14. The entry for device control is provided through a keyboard 15. At the beginning of the measurement and monitoring cycle a calibration routine is started through the control and processing unit 13. Thus, the pressure in the pressure cushion is slowly increased through the pump 9 and the diastolic and systolic blood pressure of the patient is determined through the oscillometric sensor 11. Simultaneously the pulse transit times and the pulse wave signal form are determined through at least two of the parallel PVDF foil strips 1 and the measurement device for determining the systolic and diastolic blood pressure is calibrated by associating the pulse transit time values and the pulse wave signal form with the oscillometric pressure values determined for the systole and diastole from the pressure values determined in the pressure cushion 8 and measured in the pressure sensor 10. The calibration process is performed through at least two calibration measurements, e.g. in a resting state of the patient and after a short movement phase of the patient for increasing the blood pressure. During the calibration process the threshold value of the systolic and diastolic blood pressure can be determined for initiating a possible alarm function. The pressure loading of the pressure cushion 8 is performed in an automated manner in that an oscillometric sensor 11 detects the pulse oscillation amplitudes and forwards them as an electric signal to a control and processing unit 13, where it is determined through a threshold value inquiry of the pulse oscillation amplitude whether the pressure in the pressure cushion corresponds to the diastolic or systolic blood pressure. When the threshold value is lower or higher the control and processing unit 13 causes the pump 9 to adapt the pressure in the pressure cushion 8. The oscillometric sensor 11 can be attached to the elastic membrane of the pressure cushion 8. The pressure in the pressure cushion 8 is received by a pressure sensor 10 and processed and stored in the control and processing unit 13 as a diastolic or systolic blood pressure for calibrating the measurement arrangement.

In a normal measurement and operating mode the pulse transition time values and the pulse wave signal forms are continuously measured through the pulse wave sensor 12 and transmitted to the control and processing unit 13 without pressure loading the arm jacket 7 which causes discomfort to the patient, wherein the conversion to systolic and diastolic blood pressures and their storage is performed in the control and processing unit 13. When exceeding an adjustable threshold value for the diastolic and systolic blood pressure an alarm function can be triggered, wherein the alarm function can either be incorporated in the control and processing unit 13 or is provided through the data interface 17 through an external device. The data interface 17 can be configured e.g. as a pluggable data cable or as a radio interface. Through the data interface 17 the blood pressure values can also be transmitted to external devices like a PC for further processing.

REFERENCE NUMERALS AND DESIGNATIONS

1 PVDF foil strip configured as piezo electric material with metal coating on bottom side
2 polyimide protective foil
3 flexible polyimide circuit board
4 rigid carrier circuit board configured as sensor base element
5 milled cavity
6 amplifier electronics
7 arm jacket at upper arm of patient
8 pressure cushion filled with measuring liquid
9 pump for pressure loading the pressure cushion
10 pressure sensor for pressure measurement in the pressure cushions
11 oscillometric sensor for calibration measurement of blood pressure
12 pulse wave sensor with amplifier electronics
13 control and processing unit with CPU and memory
14 LCD foil as display device
15 keyboard as entry device
16 upper arm of patient
17 data interface
18 hook and loop closure

What is claimed is:

1. A non-invasive piezo electric sensor for improved measurement of mechanical parameters and with improved measurement signal sensitivity and temperature stability for measuring pressures that vary with respect to space and time and for determining a position and propagation velocity of a pressure fluctuation and of pressure waves, the non-invasive piezo electric sensor comprising:
at least two parallel strips that are arranged parallel to each other in a measurement plane and that are each made from a piezo electric material coated with a protective foil;
at least one sensor base element;
at least one cavity between the piezo electric material and the at least one sensor base element; and
at least one piece of amplifier electronics,
wherein the at least two parallel strips and a flexible circuit board configured as a measurement membrane laminate are glued onto the at least one sensor base element, so that the at least two parallel strips and flexible circuit board are tensed in one dimension in a direction of a piezo-dipole orientation and wherein the at least one cavity is provided between the piezo electric material mounted under tension in the measurement plane and the at least one sensor base element through a recess/milled recess,
wherein the protective foil is arranged to be an outer surface of the non-invasive piezo electric sensor that can contact a surface of an object to be measured,
wherein a piezo electric foil is used for the piezo electric material for the non-invasive piezo electric sensor,
wherein a metal coated polyvinylidenfluoride foil is used for the piezo electric foil,
wherein the protective foil of the piezo electric material is configured as a polyimide foil,
wherein the at least one sensor base element is configured as a rigid carrier board,
wherein the at least one piece of amplifier electronics of the non-invasive piezo electric sensor are attached directly to the rigid carrier circuit board,
wherein the piezo electric material of the non-invasive piezo electric sensor is glued onto a flexible circuit board,
wherein the flexible circuit board is configured as a polyimide circuit board,
wherein the non-invasive piezo electric sensor comprises a control and processing unit configured for detection and processing of a systolic and diastolic blood pressure and of a pulse frequency in an automated manner,
wherein the non-invasive piezo electric sensor is capable of being used for non invasive low impact continuous detection and processing of the pulse frequency for humans and animals,
wherein measurement of the systolic and the diastolic blood pressure is performed by determining a pulse wave velocity in an artery of a human being,
wherein the pulse wave velocity is determined from pulse wave signals,
wherein the pulse wave signals are sensed by the non-invasive piezo electric sensor,
wherein measurement of the pulse frequency is performed from the pulse wave signals through the non-invasive piezo electric sensor,
wherein a calibration for determining the systolic and the diastolic blood pressures is performed by the control and processing unit at a beginning of a measurement and monitoring cycle in that for at least two calibration measurements with different blood pressures, a jacket pressure of a pressure loadable jacket is increased to a value above systolic blood pressure at the beginning of the measurement and monitoring cycle and thus the blood pressure values are derived according to a Riva-Rocci-Method using the values of the pulse wave velocity and the pulse wave signals, and
wherein two measurement membrane laminate layers disposed on top of one another and the at least two parallel strips are aligned perpendicular to one another and are adapted to facilitate a two dimensional determination of the position and the propagation velocity of pressure fluctuations and pressure waves and measurement values that are derivable there from for a random angular placement of the non-invasive piezo electric sensor at a measurement location.

2. The non-invasive piezo electric sensor according to claim 1, wherein the two measurement membrane laminate layers disposed adjacent to one another whose at least two parallel strips are aligned perpendicular to one another are adapted to facilitate a two dimensional determination of the position and propagation velocity of pressure fluctuations and pressure waves and measurement values derivable there from, for the random angular placement of the non-invasive piezo electric sensor at the measurement location.

3. A non-invasive piezo electric sensor for improved measurement of mechanical properties and with improved measurement signal sensitivity and temperature stability for measuring pressures that vary with respect to space and time and for determining a position and propagation velocity of a pressure fluctuation and of pressure waves, the non-invasive piezo electric sensor comprising:
at least two parallel strips that are arranged parallel to each other in a measurement plane and that are each made from a piezo electric material coated with a protective foil;
at least one sensor base element;

at least one cavity between the piezo electric material and the at least one sensor base element; and at least one piece of amplifier electronics, wherein the at least two parallel strips and a flexible circuit board configured as a measurement membrane laminate are glued onto the at least one sensor base element, so that the at least two parallel strips and flexible circuit board are tensed in one dimension in a direction of a piezo-dipole orientation and wherein the at least one cavity is provided between the piezo electric material mounted under tension in the measurement plane and the at least one sensor base element through a recess/milled recess, wherein the protective foil is arranged to be an outer surface of the non-invasive piezo electric sensor that can contact a surface of an object to be measured, wherein a metal coated polyvinylidenfluoride foil is used for the piezo electric material for the non-invasive piezo electric sensor, and wherein two measurement membrane laminate layers disposed on top of one another whose at least two parallel strips are aligned perpendicular to one another are adapted to facilitate a two dimensional determination of the position and the propagation velocity of pressure fluctuations and pressure waves and measurement values that are derivable there from for a random angular placement of the non-invasive piezo electric sensor at a measurement location.

4. The non-invasive piezo electric sensor according to claim 3, wherein the two measurement membrane laminate layers disposed adjacent to one another whose at least two parallel strips are aligned perpendicular to one another are adapted to facilitate a two dimensional determination of the position and propagation velocity of pressure fluctuations and pressure waves and measurement values derivable there from, for the random angular placement of the non-invasive piezo electric sensor at the measurement location.

5. A non-invasive piezo electric sensor for improved measurement of mechanical parameters and with improved measurement signal sensitivity and temperature stability for measuring pressures that vary with respect to space and time and for determining a position and propagation velocity of a pressure fluctuation and of pressure waves, the non-invasive piezo electric sensor comprising:

at least two parallel strips that are arranged parallel to each other in a measurement plane and that are each made from a piezo electric material coated with a protective foil;

at least one sensor base element;

at least one cavity between the piezo electric material and the at least one sensor base element; and at least one piece of amplifier electronics, wherein the at least two parallel strips and a flexible circuit board configured as a measurement membrane laminate are glued onto the at least one sensor base element, so that the at least two parallel strips and flexible circuit board are tensed in one dimension in a direction of a piezo-dipole orientation and wherein the at least one cavity is provided between the piezo electric material mounted under tension in the measurement plane and the at least one sensor base element through a recess/milled recess, wherein the protective foil is arranged to be an outer surface of the non-invasive piezo electric sensor that can contact a surface of an object to be measured, and wherein two measurement membrane laminate layers disposed on top of one another whose at least two parallel strips are aligned perpendicular to one another are adapted to facilitate a two dimensional determination of the position and the propagation velocity of pressure fluctuations and pressure waves and measurement values that are derivable there from for a random angular placement of the non-invasive piezo electric sensor at a measurement location.

6. The non-invasive piezo electric sensor according to claim 5, wherein the two measurement membrane laminate layers disposed adjacent to one another whose at least two parallel strips are aligned perpendicular to one another are adapted to facilitate a two dimensional determination of the position and propagation velocity of pressure fluctuations and pressure waves and measurement values derivable there from, for the random angular placement of the non-invasive piezo electric sensor at the measurement location.

* * * * *